United States Patent
Chang et al.

(10) Patent No.: US 7,314,880 B2
(45) Date of Patent: Jan. 1, 2008

(54) CARDIOPROTECTIVE DELTA OPIOID RECEPTOR AGONISTS AND METHODS OF USING SAME

(75) Inventors: Kwen-Jen Chang, Chapel Hill, NC (US); William Pendergast, Durham, NC (US); Peter J. Gengo, Sunnyvale, CA (US); Xin Ma, Carrboro, NC (US)

(73) Assignee: Mount Cook Biosciences, Inc., New York, NY (US)

( * ) Notice: Subject to any disclaimer, the term of this patent is extended or adjusted under 35 U.S.C. 154(b) by 372 days.

(21) Appl. No.: 10/749,437

(22) Filed: Dec. 31, 2003

(65) Prior Publication Data

US 2004/0171622 A1 Sep. 2, 2004

Related U.S. Application Data

(60) Provisional application No. 60/437,728, filed on Jan. 2, 2003.

(51) Int. Cl.
*A61K 31/495* (2006.01)
*A61K 31/517* (2006.01)
*A61K 31/496* (2006.01)

(52) U.S. Cl. .............................. 514/255.04; 514/266.4; 514/253.01

(58) Field of Classification Search ............. 514/266.4, 514/255.4, 253.01, 282, 252.13
See application file for complete search history.

(56) References Cited

U.S. PATENT DOCUMENTS

| | | | | |
|---|---|---|---|---|
| 5,656,420 A | * | 8/1997 | Chien ........................ | 435/1.2 |
| 5,658,908 A | * | 8/1997 | Chang et al. ........... | 514/252.13 |
| 5,854,249 A | * | 12/1998 | Chang et al. ........... | 514/252.13 |
| 6,026,817 A | | 2/2000 | Clemens | |
| 6,103,722 A | | 8/2000 | Schultz et al. | |
| 6,200,978 B1 | | 3/2001 | Maw et al. | |
| 6,262,062 B1 | | 7/2001 | Clemens | |
| 6,444,679 B1 | * | 9/2002 | Liras et al. .................. | 514/256 |
| 6,503,905 B1 | * | 1/2003 | Liras et al. ............... | 514/231.2 |
| 6,645,938 B2 | * | 11/2003 | Oeltgen et al. ............... | 514/13 |
| 6,919,350 B2 | * | 7/2005 | Chang et al. ................ | 514/282 |
| 6,924,288 B2 | * | 8/2005 | Chang .................... | 514/252.13 |
| 6,960,609 B2 | * | 11/2005 | McHardy et al. ........... | 514/406 |
| 2002/0045636 A1 | | 4/2002 | Clemens | |
| 2002/0052007 A1 | | 5/2002 | Chang et al. | |
| 2003/0186872 A1 | | 10/2003 | Chang et al. | |
| 2004/0002503 A1 | | 1/2004 | Chang et al. | |

FOREIGN PATENT DOCUMENTS

WO WO 99/01438 A1 1/1999

OTHER PUBLICATIONS

"NIH Heart Disease & Stroke Research: Fact Sheet", American Heart Association 2004.*
Cardiovascular Disease:Treatment for Stroke, Standford Hospital & Clinics, 2003.*
"Heart Disease", Charlotte E. Grayson, WebMD, 2004.*
"Acute Congestive Heart Failure", Thomas N. Levin, Postgraduate Medicine, vol. 101, No. 1, 1997.*
Ito et al., "U-92032, a T-type $Ca^{2+}$ channel blocker and antioxidant, reduces neuronal ischemic injuries", European Journak of Pharmacology, (1994), 257, 203-325.
Patel, Hemal H., et al. "BW373U86, a δ Opioid Agonist, Partially Mediates Delayed Cardioprotection via a Free Radical Mechanism that is Independent of Opioid Receptor Stimulation." Journal of Molecular Cell Cardiology, vol. 33, (2001), pp. 1455-1465.
Patel, Hemal H., et al. "Delta opioid agonists and volatile anesthetics facilitate cardioprotection via potentiation of $K_{ATP}$ channel opening." FASEB J., vol. 16, (2002),pp. 1468-1470.
Lasukova, T. V., et al. "Effect of in Vivo and in Vitro Stimulation of $δ_1$-Opioid Receptors on Myocardial Resistance to Arrhythmogenic Action of Ischemia and Reperfusion." Bulletin of Experimental Biology and Medicine, No. 4, (2002), pp. 359-362.
Murry, C.E. et al. "Preconditioning with ischemia: a delay of lethal cell injury in ischemic myocardium." Abstract from Circulation, vol. 74, No. 5, (1986), pp. 1124-1136.

* cited by examiner

Primary Examiner—Brian Kwon
(74) Attorney, Agent, or Firm—Marianne Fuierer; Eric F. Wagner; Moore & Van Allen PLLC

(57) ABSTRACT

The present invention relates to compositions and methods of treatment for cardioprotection through the use of non-peptidic delta opioid receptor agonist compound(s) that mediate cardioprotective effects of ischemic preconditioning. The compounds are used to reduce injury associated with ischemia and reperfusion of cardiac tissue. Further, the compounds may be used in solutions preserving the viability of an isolated organ.

18 Claims, 2 Drawing Sheets

Occlusion-reperfusion control

US 7,314,880 B2

CARDIOPROTECTIVE DELTA OPIOID RECEPTOR AGONISTS AND METHODS OF USING SAME

CROSS-REFERENCE TO RELATED APPLICATIONS

This application claims priority from U.S. Provisional Patent Application No. 60/437,728 filed on Jan. 2, 2003, the disclosure of which is hereby incorporated by reference herein for all purposes.

BACKGROUND OF THE INVENTION

1. Field of the Invention

The present invention relates to compositions and methods of treatment for cardioprotection, and more particularly, to non-peptidic delta opioid receptor agonist compound(s) that mediate cardioprotective effects of ischemic preconditioning.

2. Description of the Related Art

Tissues deprived of blood and oxygen undergo ischemic necrosis or infarction with possible irreversible organ damage. In patients that survive a myocardial infarction exhibit a decreased viable myocardium due to ischemic damage. However, people who have angina previous to a heart attack, due to reduced oxygen flow to the heart muscle, show less tissue damage of the myocardium relative to those without angina. Thus, brief episodes of ischemia have the effect of protecting the myocardium from ischemic damage.

Ischemic preconditioning (PC) is a phenomenon, widely demonstrated in many species, including man, whereby the myocardium is protected from a major ischemic event by prior brief periods of ischemia or hypoxia followed by reperfusion or reoxygenation. The use of short duration, transient ischemia to protect against damage from a subsequent and more prolonged ischemic event has been demonstrated by Murry, et al. (*Circulation*, 1986: 74: 1124-1136). Test results show a reduction of tissue necrosis by approximately 30% in canine hearts that have been pretreated with short periods of ischemia prior to a major long-term event. The phenomenon of ischemic preconditioning has become of great clinical interest for treatment of patients with ischemic heart disease.

Ischemic preconditioning requires a physical reduction of the blood supply, which can be difficult or impractical for most patients. It has been found that exercise has the effect of ischemic preconditioning lasting approximately 24 hours but many patients are not physically capable of reaching the level of cardiac output required to reap the benefits of ischemic preconditioning. Intermittent ischemia induced by aortic cross-clamping prior to coronary bypass surgery has been used as a clinical application of ischemic preconditioning. It has been found that following a surgical procedure, cardiac output was significantly higher in patients who had myocardial preconditioning. Also preconditioned patients exhibited improved postoperative hemodynamics relative to patients without preconditioning. However, multiple potential problems can be associated with aortic cross clamping to effectuate reduced blood supply to the cardiac muscle, and thus it is desirable to have a treatment that potentiates ischemic preconditioning by pharmacological means.

It has been determined that a number of membrane receptors are involved in preconditioning including opioid receptors. The three main opioid receptor subtypes are μ, κ and δ. Delta opioid receptor stimulation mimics natural hibernation even in non-hibernating animals and has been reported to enhance tissue survival when oxygen delivery to the tissue is minimal. As such, delta opioid receptor stimulation has been shown to be involved in ischemic preconditioning. A number of studies have been conducted using peptidic and non-peptidic delta opioid receptor agonists to induce the effects of ischemic preconditioning. Schultz and Gross (U.S. Pat. No. 6,103,722) tested numerous non-peptidic delta opioid receptor compounds that exhibited ischemic preconditioning effects including (−)-2-Methyl-4a.α-(3-hydroxyphenyl)-1,2,3,4,4a,5,12,12a.β-octahydro-quinolino [2,3] isoquinoline (TAN67(−)); (±)-4-((αR*)-α-((2S*,5R*)-4-allyl-2,5-dimethyl-1-piperazinyl)-3-hydroxybenzyl)-N,N diethylbenzamide (BW373U86); and (+)-4-[(αR)-α-((2S,5R)-4-allyl-2,5-dimethyl-1-piperazinyl)-3-methoxybenzyl]-N,N-diethylbenzamide (SNC80). However, these non-peptidic compounds are not without problems, especially because these compounds are considered analgesics and several of the compounds are known to cause seizures in the dosed subject due to the passage of these compounds over the blood brain barrier.

As such, it is desirable to have a treatment that potentiates ischemic preconditioning by pharmacological means, which avoids the problems associated with reduced blood supply to the cardiac muscle and the potential of seizures caused by administration of some delta opioid receptor agonist compounds.

SUMMARY OF THE INVENTION

Present invention relates in one aspect to a therapeutic composition for combating ischemic damage and/or effectuating ischemic preconditioning, the composition comprising an effective amount of a diarylmethylpiperazine compound of the formula:

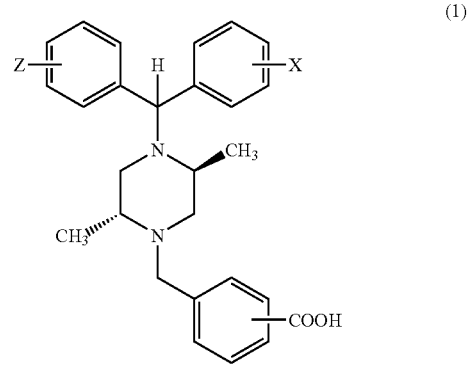

(1)

wherein:
Z is selected from the group consisting of:
  hydrogen;
  halogen;
  $C_1$-$C_6$ alkyl, $C_2$-$C_6$ alkenyl, $C_2$-$C_6$ alkynyl;
  $C_1$-$C_6$ haloalkyl;
  $C_1$-$C_6$ alkoxy;
  $C_3$-$C_6$ cycloalkoxy;
  sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and an $C_1$-$C_6$ alkyl moiety, or $C_5$-$C_{10}$ aryl;
  sulfoxides of the formula $SOR^8$ where $R^8$ is the same as above;

sulfones of the formula $SO_2R^8$ where $R^8$ is the same as above;

nitrile;

$C_1$-$C_6$ acyl;

alkoxycarbonylamino (carbamoyl) of the formula $NHCO^2R^8$ where $R^8$ is the same as above;

carboxylic acid, or an ester, amide, or salt thereof;

aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C;

carboxamides of the formula $CONR^9R^{10}$ where $R^9$ and $R^{10}$ are the same as above, or $C_2$-$C_{30}$ peptide conjugates thereof; and sulfonamides of the formula $SO_2NR^9R^{10}$ where $R^9$ and $R_{10}$ are the same as above; and X is selected from the group consisting of hydrogen, hydroxyl, halogen and alkoxy, or a pharmaceutically acceptable ester or salt thereof.

Another aspect of the present invention relates to a method of reducing ischemic damage in a subject comprising: administering an effective amount of a therapeutic composition comprising a diarylmethylpiperazine compound of the formula:

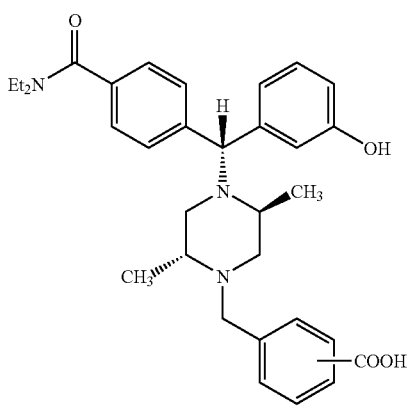

(2)

or a pharmaceutically acceptable salt or ester thereof.

Yet another aspect of the invention relates to a method of reducing ischemic damage and/or effectuating ischemic precondition in a subject, the method comprising: administering to said subject an effective amount of a delta opioid receptor of the formula:

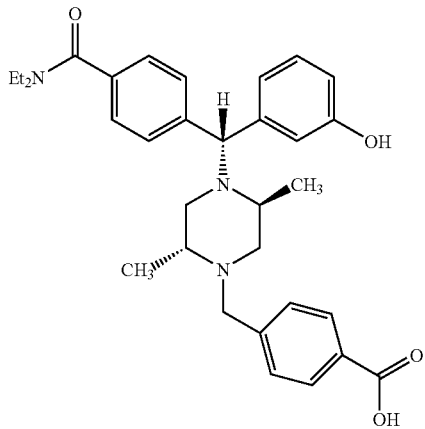

(3)

or a pharmaceutically acceptable salt or ester thereof.

Preferably, the diarylmethylpiperazine compounds of the present invention are non-analgesic compounds that act predominately on peripheral delta opioid receptors. The diarylmethylpiperazine compounds may be administered during several different effective time frames including: concurrently with the onset of an ischemic event; prior to onset of ischemia as a preventive regimen to prevent disease progression in individuals who are in the symptomatic phase of ischemic heart disease; pre-surgery in a patient that may be at risk of a blood clot or other types of cardiac ischemia; or after the onset of an ischemic event.

The efficacy of the compounds of the present invention can be evaluated by using noninvasive clinical imaging methods, such as magnetic resonance imaging (MRI), of the affected region to determine the size of the damaged area.

In another aspect, the present invention relates to solutions that preserve viability of an isolated organ comprising the compound of the formula:

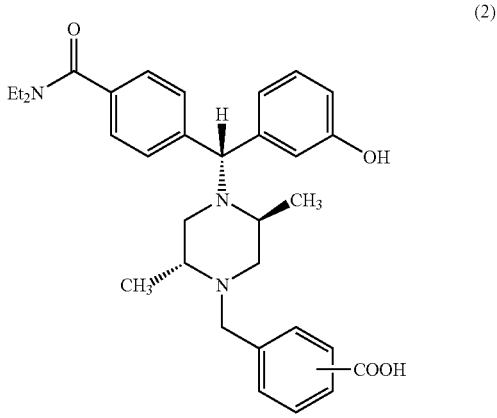

(2)

or a pharmaceutically acceptable salt or ester thereof, at a concentration effective to protect the organ from ischemic injury. The isolated organ may include, but is not limited to heart, liver, kidney, cornea and/or lung.

The therapeutic compositions may be administered by any suitable administrative mode, e.g., an administration modality selected from the group including oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

A still further aspect of the present invention relates to a method of protecting against a prolonged ischemia attack and reperfusion injury in a mammal, the method comprising administering an effective amount of a delta opioid receptor agonist of the formula:

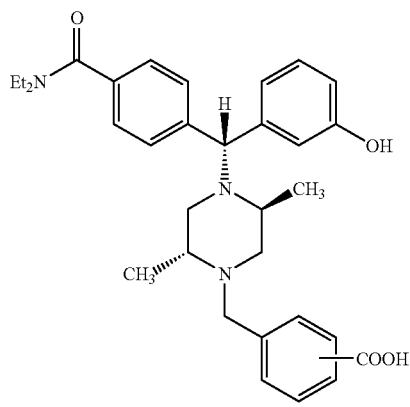

(2)

or pharmaceutically acceptable esters and salts; and a second compound that has an anti-ischemic effect, including arginine hydrochloride, which is used to counteract the decline in cardiac function following an ischemic event, and other latent sources of nitric oxide that serve a similar purpose.

Various other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1A:
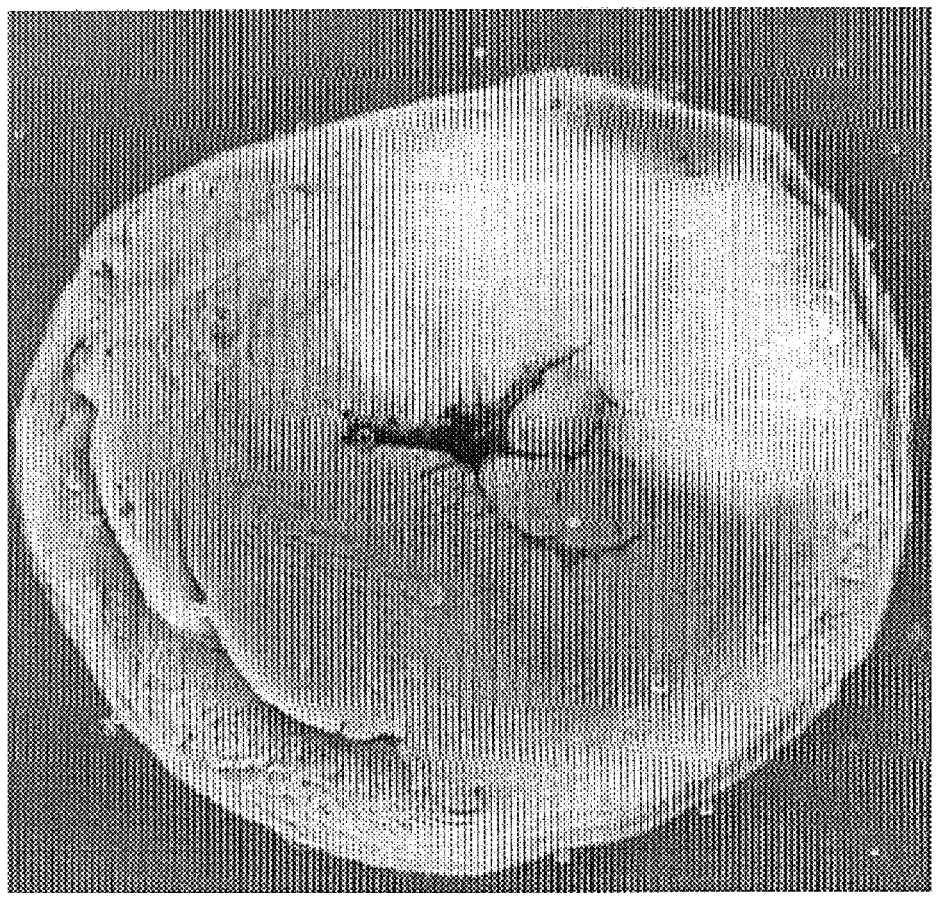
FIG. 1a and FIG. 1b show histological samples of infarction size in control and treated animals.

In one broad aspect of the present invention, a diarylmethylpiperazine compound as hereinafter more fully described, is administered to a subject to mediate ischemic preconditioning thereby providing reduced tissue necrosis, improved post-ischemic contractile function and decreased occurrence of post-ischemic dysrhythmia. The treatment in accordance with the present invention may advantageously include mono-therapy treatment wherein compounds of the present invention are administered as singular therapeutic agents in therapeutic compositions, or co-therapy treatment, wherein a compound in accordance with the present invention is administered contemporaneously, e.g., simultaneously, or sequentially, with another cardiac therapeutic agent that is administered to mediate a corrective or protective cardiac response. Other cardiac therapeutic agents may include, but are not limited to nitrates, beta-adrenergic blockers, calcium channel antagonists, ACE inhibitors, non-peptide angiotensin II antagonists, IIb/IIIa antagonists and aspirin.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethylpiperazine compound for its intended utility (examples of substituents for substituted alkyl groups include halogen (e.g., fluoro, chloro, bromo, and iodo), amino, amido, $C_1$-$C_4$ alkyl, $C_1$-$C_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethylpiperazine compound for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethylpiperazine delta opioid receptor agonist for its intended utility. Examples of substituents for substituted aryl groups include hydrogen, one or more of halogen (e.g., fluoro, chloro, bromo, and iodo), amino, amido, $C_1$-$C_4$ alkyl, $C_1$-$C_4$ alkoxy, nitro, trifluoromethyl, hydroxy, hydroxyalkyl containing a $C_1$-$C_4$ alkyl moiety, etc.

Examples of pharmaceutically acceptable esters of compounds of formulae (1), (2) and (3) include carboxylic acid esters of the hydroxyl group in the compounds of formula (1) where X=OH and formulae (2) and (3) in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl) aminocarbonyl); and inorganic esters (e.g. mono-, di- or triphosphate).

Examples of pharmaceutically acceptable salts of the compounds of formulae (1), (2) and (3) include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4^+$, or $NR'_4{}^+$ (wherein R' is for example a $C_{1-4}$ alkyl group).

The present invention also contemplates pharmaceutical formulations, both for veterinary and for human medical use, which comprise as the active agent one or more diarylmethylpiperazine compound(s) of the present invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The diarylmethylpiperazine compound(s) is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

When the diarylmethylpiperazine compound(s) is utilized in a formulation comprising a liquid solution, the formulation advantageously may be administered parenterally. When the diarylmethylpiperazine compound(s) is employed in a liquid suspension formulation or as a powder in a biocompatible carrier formulation, the formulation may be advantageously administered orally, rectally, or bronchially.

When the diarylmethylpiperazine compound(s) is utilized directly in the form of a powdered solid, it may advantageously be administered orally. Alternatively, it may be administered bronchially, via nebulization of the powder in a carrier gas, to form a gaseous dispersion of the powder that is inspired by the patient from a breathing circuit comprising a suitable nebulizer device.

In some applications, it may be advantageous to utilize the diarylmethylpiperazine compound(s) in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the diarylmethylpiperazine compound(s) of the present invention may conveniently be presented in unit dosage forms and may be prepared by any of the methods well known in the art of pharmacy. Such methods generally include the step of bringing the diarylmethylpiperazine compound(s) into association with a carrier that constitutes one or more accessory ingredients. Typically, the formulations are prepared by uniformly and intimately bringing the diarylmethylpiperazine compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the diarylmethylpiperazine compound(s) as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the diarylmethylpiperazine compound(s) being in a free-flowing form such as a powder or granules which optionally is mixed with a binder, disintegrant, lubricant, inert diluent, surface active agent, or discharging agent. Molded tablets comprised of a mixture of the powdered diarylmethylpiperazine compound(s) with a suitable carrier may be made by molding in a suitable machine.

Syrup may be made by adding compounds of the present invention to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of a compound of the present invention, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the compounds of the present invention with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise at least one compound of the present invention dissolved or suspended in one or more media, such as mineral oil, petroleum, polyhydroxy alcohols, or other bases used for topical pharmaceutical formulations.

Transdermal formulations may be prepared by incorporating a compound of the present invention in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

In some cases, in order to prolong the effect of a diarylmethylpiperazine compound of the present invention, it is desirable to slow the absorption of the diarylmethylpiperazine compound(s) from subcutaneous or intramuscular injection. This may be accomplished by the use of a liquid suspension of crystalline or amorphous material having poor water solubility. The rate of absorption of the diarylmethylpiperazine compound(s) then depends upon its rate of dissolution, which, in turn, may depend upon crystal size and crystalline form. Alternatively, delayed absorption of a parenterally administered diarylmethylpiperazine compound(s) is accomplished by dissolving or suspending the drug in an oil vehicle.

Injectable depot forms may be prepared by forming microencapsule matrices of at least one compound of the present invention in biodegradable polymers such as polylactide-polyglycolide. Depending on the ratio of active ingredient to polymer, and the nature of the particular polymer employed, the rate of release of the active ingredient can be controlled. Examples of other biodegradable polymers include poly(orthoesters) and poly(anhydrides). Depot injectable formulations are also prepared by entrapping the active ingredient in liposomes or microemulsions, which are compatible with body tissue. The injectable materials can be sterilized for example, by filtration through a bacterial-retaining filter.

Depending on the specific condition to be treated, animal subjects may be administered compounds of the present invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific condition involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms (μg) to 100 milligrams (mg) per kilogram body weight of the recipient per day, preferably in the range of 50 μg to 75 mg per kilogram body weight per day, and most preferably in the range of 100 μg to 50 mg per kilogram body weight per day. The desired dose may be presented as two, three, four, five, six, or more sub-doses administered at appropriate intervals throughout the day, especially if surgery is imminent. Additionally, the timing of a single dose is preferably up to four hours after an onset of an ischemic attack. The desired dose may be repeated multiple times to render the heart muscle more resistant to any subsequent longer ischemia attacks.

The following examples are illustrative of synthetic procedures that may be advantageously utilized to synthesize compounds of the present invention.

EXAMPLE 1

4-{(2R, 5S)-4-[(R)-(4-Diethylcarbamoylphenyl)(3-hydroxyphenyl)methyl]-2,5-dimethyl-1-piperazinylmethyl}benzoic acid

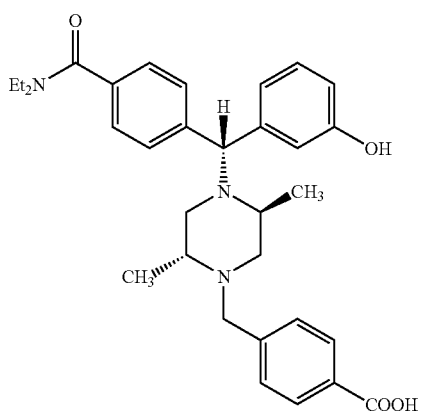

A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates were combined and the solvent removed under reduced pressure to give 669 g (98.4%) of 3-bromophenoxy-tert-butyldimethylsilane as a clear pale yellow liquid. $^1$H NMR (CDCl$_3$, 300 MHz): δ7.1 (m, 2H); 7.0 (br s, 1H); 6.75 (m,1H); 1.0 (s, 9H); 0.2 (s, 6H).

3-tert-Butyldimethylsilyloxyphenylmagnesium bromide was formed by the slow addition of a mixture 3-bromophenoxy-tert-butyldimethylsilane (45.97 g, 160 mmol) and 1,2-dibromoethane (6.01 g, 32 mmol) in 150 mL of inhibitor-free anhydrous tetrahydrofuran to a mixture of magnesium turnings (4.28 g, 176 mmol) in 400 mL of inhibitor-free anhydrous tetrahydrofuran at reflux. After stirring for one hour at reflux the clear, light brown solution was cooled to room temperature.

4-Carboxybenzaldehyde (100.3 g, 0.67 mol) was dissolved/suspended in toluene (1200 mL), N, N-dimethylformamide (0.15 mL) was added and the suspension was stirred during the dropwise addition of thionyl chloride (53.5 mL, 87.2 g, 0.73 mol). The reaction mixture was heated to reflux under nitrogen and stirred for 2 hours, during which time most, but not all, of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M hydrochloric acid (2×600 mL), water (2×300 mL), dilute sodium carbonate solution (saturated: H$_2$O/1:1, 2×600 mL), water (2×300 mL) and saturated sodium chloride solution (300 mL). The organic layer was separated, dried over anhydrous sodium sulfate and evaporated to yield 4-formyl-N, N-diethylbenzamide as a pale brown oil, which was used without further purification. (Yield: 115.7 g, 84%).

In a 3 L round bottom flask fitted with a condenser and Dean-Stark trap were combined 4-formyl-N, N-diethylbenzamide (20.53 g, 100 mmol), benzotriazole (11.91 g, 100 mmol), and (2R,5S)-1-allyl-2,5-dimethylpiperazine (15.43 g, 100 mmol, Chirotech Technology, Ltd., Cambridge, England) with 1000 mL of toluene. The reaction was heated to reflux under nitrogen until no additional water was observed in the trap (ca. 3 hours). The reaction was cooled to room temperature and concentrated under vacuum to leave a volume of approximately 300 mL. Anhydrous tetrahydrofuran (500 mL) was added to the benzotriazole adduct under nitrogen and stirred to give a complete solution. This solution was added to the solution of 3-tert-butyldimethylsilyloxyphenylmagnesium bromide (above) at room temperature via double-ended needle. After stirring for 1.5 hours, the reaction was quenched by the addition of saturated aqueous ammonium chloride solution (50 mL) and stirred for 15 minutes. Anhydrous magnesium sulfate (50 g) was added, stirred for 1.5 hours, and the reaction was filtered. The solvent was removed under reduced pressure and the residue was dissolved in ethyl acetate (1000 mL). The ethyl acetate solution was washed with 1 M sodium hydroxide (5×400 mL), water (4×400 mL), and saturated aqueous sodium chloride solution (400 mL). The organic layer was dried over anhydrous magnesium sulfate and the solvent was removed to give a dark oil. The oil was dissolved in 500 mL of tetrahydrofuran and 300 mL of 3 M hydrochloric acid and stirred for 1.5 hours at room temperature. The reaction was diluted with water (300 mL) and concentrated under vacuum to about half the original volume. This solution was extracted with pentane (2×500 mL). The aqueous layer was adjusted to pH 8-9 with 5 M sodium hydroxide and extracted with ethyl acetate (250 mL). The layers were separated and the aqueous portion was extracted with more ethyl acetate (250 mL). The combined organic extracts were washed with saturated aqueous sodium chloride solution, dried over anhydrous sodium sulfate, and the solvent was removed under reduced pressure to give a brown oil. This residue was dissolved in ethyl acetate (25 mL), seeded with crystals of the authentic compound and allowed to crystallize overnight (Michael J. Bishop and Robert W. McNutt, Seed Crystals Obtained From Hot 2-propanol With Addition of Water, *Bioorg. Med. Chem. Lett.* (1995), 5, 1311-14)). The crystals were filtered and washed sparingly with cold ethyl acetate.

Drying under 5 mm Hg at room temperature yielded 4-[(R)-((2S,5R)-4-allyl-2,5-dimethyl-1-piperazinyl)(3-hydroxyphenyl)methyl]-N,N-diethylbenzamide as white crystals (14.15 g, 32.5% from 4-formyl-N,N-diethylbenzamide). The product showed a single peak on HPLC (Zorbax RX C8, 4.6 mm×25 cm, isocratic 40% 0.01 M $NH_4OAc$ in MeOH, 3 min; linear gradient to 100% MeOH, 45 min; isocratic MeOH, 5 min; 1.0 mL/min; $\lambda_{obs}$=210 nm, Rt=32.21 min). Calc. for $C_{27}H_{37}N_3O_2$: %C, 74.45; H, 8.56; N, 9.65. Found: %C, 74.48; H, 8.60; N, 9.62. $^1$H NMR ($CDCl_3$, 300 MHz): δ 7.42 (d, J=8.1 Hz, 2H); 7.28 (d, J=8.4 Hz, 2H); 7.08 (t, J=7.8 Hz, 1H); 6.64-6.57 (m, 3H); 5.94-5.83 (m, 1H); 5.22 (d, J=8.7 Hz, 1H); 5.18 (s, 1H); 5.14 (br s, 1H); 3.60-3.47 (m, 2H); 3.42 (dd, J=5.2, 13.7 Hz, 1H); 3.37-3.20 (br m, 2H); 2.91 (dd, J=8.1, 13.5 Hz, 1H); 2.85 (dd, J=2.6, 11.4 Hz, 1H); 2.70-2.47 (m, 3H); 2.17 (t, J=10.7 Hz, 1H); 1.98 (t, J=11.1 Hz, 1H); 1.23 (m, 3H); 1.14 (d, J=6.1 Hz, 3H, overlapping with m, 3H); 1.02 (d, J=6.2 Hz, 3H).

A solution of 4-[(R)-((2S,5R)-4-allyl-2,5-dimethyl-1-piperazinyl)(3-hydroxyphenyl)-methyl]-N,N-diethylbenzamide (10.89 g, 25 mmol) and thiosalicylic acid (4.63 g, 30 mmol) in anhydrous tetrahydrofuran (50 mL) was stirred with a catalyst solution prepared by dissolution of bis(dibenzylidineacetone)palladium (0.718 g, 1.25 mmol) and 1,4-bis(diphenylphosphino)butane (0.533 g, 1.25 mmol) in tetrahydrofuran (10 mL) at room temperature under nitrogen for 1.5 hours. (J.P. Genet, S. Lemaire-Audoire, M. Savignac, *Tetrahedron Letters*, 36, 1267-1270 (1995)). The reaction mixture was concentrated under reduced pressure and the residue was partitioned between ethyl acetate (150 mL) and aqueous sodium carbonate solution. The layers were separated and diethyl ether (250 mL) was added to the organic layer. This was extracted with 5% sodium carbonate solution (2×150 mL). The organic layer was diluted with pentane (500 mL) and extracted with 3 M hydrochloric acid (6×30 mL). The aqueous solution was adjusted to pH 9-10 with saturated aqueous sodium carbonate solution and extracted with methylene chloride (3×100 mL). The combined organic extracts were dried over anhydrous sodium sulfate and the solvent was removed under reduced pressure to yield 4-[(R)-((2S,5R)-2,5-dimethyl-1-piperazinyl)(3-hydroxyphenyl)methyl]-N,N-diethylbenzamide as a brittle pale yellow foam (10.24 g). The product showed a single peak on HPLC (Zorbax C-8, isocratic 40% 0.01 M $NH_4OAc$ in MeOH, 3 min; linear gradient to 100% MeOH, 45 min; isocratic MeOH, 5 min; 1.0 mL/min; $\lambda_{obs}$ =210 nm, Rt=19.24 min). Calc. for $C_{24}H_{33}N_3O_2$ 0.1 EtOAc 0.4 $CH_2Cl_2$: %C, 67.96; H, 7.96; N, 9.59. Found: %C, 67.90; H, 8.03; N, 9.54. $^1$H NMR ($CDCl_3$, 300 MHz): δ 7.42 (d, J=8.1 Hz, 2H); 7.26 (d, J=8.3 Hz, 2H); 7.11 (t, J=7.8 Hz, 1H); 6.72 (d, J=8.1 Hz, 1H); 6.65 (s, 1H); 6.59 (d, J=7.6 Hz, 1H); 5.16 (s, 1H); 4.93 (v br s, 2H); 3.51 (br m, 2H); 3.27 (br m, 2H); 3.02-2.97 (m, 1H); 2.92 (d, J=10.5 Hz, 1H); 2.66 (br d, J=8.5 Hz, 2H); 2.60-2.45 (m, 1H); 1.84 (dd, J=11.3, 8.3 Hz, 1H); 1.27-1.15 (m, 3H); 1.10 (d, J=6.1 Hz, 3H overlapping with m, 3H); 1.02 (d, J=6.1 Hz, 3H).

4-{(2R, 5S)-4-[(R)-(4-Diethylcarbamoylphenyl)(3-hydroxyphenyl)methyl]-2,5-dimethyl-1-piperazinylmethyl}benzoic acid Method A: Reductive Alkylation Glacial acetic acid (0.635 mL, 11.1 mmol) was added to a solution of 4-[(R)-((2S,5R)-2,5-dimethyl-1-piperazinyl)-(3-hydroxyphenyl)methyl]-N,N-diethylbenzamide (1.98 g, 5 mmol) and 4-carboxybenzaldehyde (1.50 g, 10 mmol) in anhydrous tetrahydrofuran (35 mL. While stirring briskly, sodium triacetoxyborohydride (2.12 g, 10 mmol) was added in 50-100 mg portions, allowing effervescence to subside after each addition. The reaction was monitored for absence of starting material by HPLC. After stirring at room temperature for 16 hours, more 4-carboxybenzaldehyde (0.75 g, 5 mmol), acetic acid (0.318 mL, 5 mmol), and sodium triacetoxyborohydride (1.06 g, 5 mmol) was added. After stirring an additional 4 hours, the reaction mixture was concentrated under reduced pressure and the residue was partitioned between ethyl acetate (50 mL) and 3 M hydrochloric acid (10 mL). The layers were separated and the organic layer was extracted again with 3 M hydrochloric acid (5×10 mL). The aqueous solution was adjusted to pH 4.5-5 with saturated aqueous sodium carbonate solution and extracted with methylene chloride (3×50 mL). The combined organic extracts were dried over anhydrous sodium sulfate and the solvent was removed under reduced pressure to yield 4-{(2R, 5S)-4-[(R)-(4-diethylcarbamoylphenyl)(3-hydroxyphenyl)methyl]-2,5-dimethyl-1-piperazinylmethyl}benzoic acid as a brittle white foam (2.34 g). The product showed a single peak on HPLC (Zorbax RX-C8, 4.6 mm×25 cm, isocratic 40% 0.01 M $NH_4OAc$ in MeOH, 3 min; linear gradient to 100% MeOH, 45 min; isocratic MeOH, 5 min; 1.0 mL/min; $\lambda_{obs}$=210 nm, Rt=13.75 min).

4-{(2R, 5S)-4-[(R)-(4-Diethylcarbamoylphenyl)(3-hydroxybenyl)methyl]-2,5-dimethyl-1-piperazinylmethyl}benzoic acid (2.09 g, 3.5 mmol) was dissolved in ethanol (6 mL) and 0.986 N hydrochloric acid (3.60 mL) was added. This solution was diluted with distilled water (30 mL), filtered, rapidly frozen, and lyophilized to give a white solid (2.17 g). Calc. for $C_{32}H_{39}N_3O_4$ 1.6 HCl 1.6 $H_2O$: %C, 62.31; H, 7.16; N, 6.81; Cl, 9.20. Found: %C, 62.32; H, 7.19; N, 6.74; Cl, 9.28. $^1$H NMR ($D_2O$+50% v/v 1-M NaOD in $D_2O$, 300 MHz): δ 7.57 (d, J=8.1 Hz, 2H); 7.17 (d, J=8.0 Hz, 2H); 7.11 (d, J=8.1 Hz, 2H); 6.99 (d, J=8.1 Hz, 2H); 6.81 (t, J=7.8 Hz, 1H); 6.30 (s, 1H); 6.29 (partially overlapped d, J=7.5, 1H); 6.13 (d, J=7.5 Hz, 1H); 4.89 (s, 1H); 3.78 (d,J=12.7 Hz, 1H); 3.22 (q, J=7.2 Hz, 2H); 3.05 (d, J=12.9 Hz, 1H); 2.95 (q, J=7.2 Hz, 2H); 2.60 (d, J=11.2 Hz, 1H);

2.35 (d, J=11.4 Hz, 1H); 2.31-2.19 (m, 2H); 1.87-1.74 (m, 2H); 0.94 (t, J=7.3 Hz, 3H); 0.87 (t, J=7.3 Hz, 3H); 0.77 (d, J=6.3 Hz, 3H); 0.75 (d, J=6.3 Hz, 3H; both doublets overlapping).

Method B: Direct Alkylation

4-[(R)-((2S,5R)-2,5-Dimethyl-1-piperazinyl)(3-hydroxyphenyl)methyl]-N,N-diethylbenzamide (1.41 g, 3.56 mmol) in acetonitrile (15 mL) was added to sodium iodide (80 mg, 0.53 mmol) and stirred during the addition of triethylamine (2.0 mL, 14.3 mmol), followed by methyl 4-(bromomethyl)benzoate (1.63 g, 7.12 mmol). The reaction mixture was sealed under nitrogen and stirred at ambient temperature for 20 hours. The reaction mixture was concentrated under reduced pressure and the residue was partitioned between ethyl acetate (50 mL) and water (25 mL). The organic layer was separated and the aqueous layer was extracted with ethyl acetate (3×20 mL). The combined organic extracts were extracted with 5% sodium carbonate solution (2×50 mL) and then water (50 mL). The organic layer was diluted with pentane (100 mL) and extracted with 1 M hydrochloric acid (5×30 mL). The aqueous solution was adjusted to pH 8.5-9 with saturated aqueous sodium carbonate solution and extracted with methylene chloride (3×50 mL). The combined organic extracts were dried over anhydrous sodium sulfate and magnesium sulfate. The solvent was removed under reduced pressure to yield a light yellow solid (1.90 g). The residue was dissolved in methylene chloride (5 mL) and applied to a pre-packaged (4×7 cm) Biotage silica gel column and eluted with a gradient of 20% to 60% solution A in B [A=ethyl acetate with 2% NH$_4$OH, B=methylene chloride]. Desired fractions containing the product [silica t.l.c. (EtOAc with 2% NH$_4$OH: CH$_2$Cl$_2$/1:1) Rf=0.39] were concentrated under reduced pressure and further dried under 2 mm Hg at room temperature to yield methyl 4-{(2R,5S)-4-[(R)-(4-diethylcarbamoylphenyl)(3-hydroxyphenyl)methyl]-2,5-dimethyl-1-piperazinylmethyl}benzoate (1.34 g) as an off-white solid. Calculated for C$_{33}$H$_{41}$N$_3$O$_4$: %C, 72.90; H, 7.60; N, 7.73. Found: %C, 72.68; H, 7.57; N, 7.64. $^1$H NMR (CDCl$_3$, 300 MHz): δ 7.95 (d, J=8.4 Hz, 2H); 7.44 (d, J=8.1 Hz, 2H); 7.37 (d, J=8.2 Hz, 2H); 7.28 (d, J=8.2 Hz, 2H); 7.14 (t, J=7.8 Hz, 1H); 6.73-6.69 (m, 2H); 6.64 (s, 1H); 6.05 (br s, 1H); 5.00 (s, 1H); 3.94 (d, J=14 Hz, 1H partially overlapping with s, 3H); 3.89 (s, 3H); 3.54 (br m, 2H); 3.29 (br m, 2H); 3.24 (d, J=14 Hz, 1H); 2.68-2.53 (m, 4H); 2.05-1.94 (m, 2H); 1.26 (br m, 3H); 1.23 (br m, 3H); 1.06 (overlapping d, J=5.9 Hz, 3H); 1.04 (overlapping d, J=5.9 Hz, 3H).

This solid (0.88 g, 1.62 mmol) was dissolved in ethanol (10 mL) and 2.5 M sodium hydroxide solution (6.4 mL, 16 mmol) was added in approximately 1 mL aliquots. The slightly turbid reaction mixture clarified about 5 min after the last addition to yield a yellow solution, which was stirred for 16 h at ambient temperature. The solution was diluted with an equal volume of water and the ethanol was removed by evaporation along with an estimated 50% of the aqueous volume. The solution was adjusted to pH 4 using 3 M hydrochloric acid. The resulting flocculent white solid was collected by filtration and washed sparingly with cold water. After air-drying the solid was further dried under vacuum of 5 mm Hg at room temperature to yield the title compound (0.90 g, 85.9%). This material was identical by HPLC to the compound made by Method A. Calc. for C$_{32}$H$_{39}$N$_3$O$_4$ 1.5 NaCl 1.6 H$_2$O: %C, 59.48; H, 6.58; N, 6.50. Found: %C, 59.50; H, 6.45; N, 6.32. $^1$H NMR ((d$_6$-DMSO+20% v/v 1-M NaOD in D$_2$O, 300 MHz); δ 0.93 (d, J=6.0 Hz, 3H); 0.98 (d, J=5.9 Hz, 3H; both doublets overlapping br m, 6H); 1.9 (m, 2H); 2.54 (m, 2H, partially obscured by DMSO); 3.13 (br m, 2H); 3.22 (d, J=14.2 Hz, 1H); 3.34 (br m, 2H); 3.71 (d, J=14.0 Hz, 1H); 4.66 (s, 1H); 5.97 (d, J=6.9 Hz,1H); 6.16 (d, J=7.9, 1H); 6.23 (s, 1H); 6.72 (t, J=7.7 Hz, 1H); 7.16 (d, J=7.8 Hz, 4H); 7.38 (d, J=8.1 Hz, 2H); 7.72 (d, J=8.1 Hz, 2H). Mass spectrum: (ESI-, DP-120V, MeOH); m/z: 529.0, (M+, 100%); 528, ((M−1)+, 57%); 512.6, ((M−17)+, 95%).

EXAMPLE 2

4-{(2R, 5S)-4-[(S)-(4-Diethylcarbamoylphenyl)(3-hydroxyphenyl)methyl]-2,5-dimethyl-1-piperazinylmethyl}benzoic acid

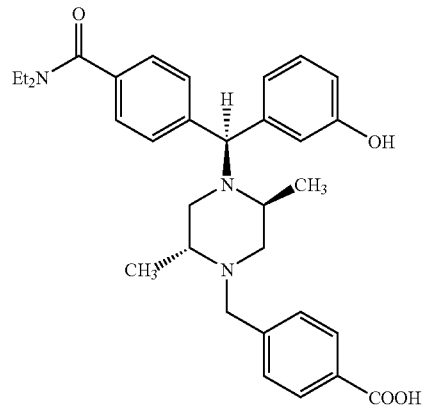

4-Carboxybenzaldehyde (100 g, 666 mmol) was weighed in a 2000 mL, 3-necked, round bottom flask and stirred under nitrogen in 1200 mL of toluene. Thionyl chloride (53.5 mL, 733 mmol) was added to the mixture, followed by the addition of 0.15 mL of dimethylformamide. A reflux condenser fitted with a calcium chloride drying tube was placed on the flask. The reaction was placed in an oil bath and heated at a bath temperature maintained below 120° C. The mixture was allowed to reflux for 1 hour after a clear solution was obtained and then cooled to room temperature. The solution was diluted with anhydrous toluene, and all volatiles were removed under vacuum.

The crude acid chloride was dissolved in 1500 mL of dry tetrahydrofuran and cooled in an ice/water bath. Diethylamine (173 mL, 1.67 mol, 2.5 equivalents) was added dropwise via an addition funnel. The cloudy solution was allowed to warm to room temperature over 1 hour and stirred overnight. The reaction mixture was filtered to remove the white crystalline diethylamine hydrochloride by-product. The crystals were washed with ethyl acetate (2×600 mL). The tetrahydrofuran filtrate was evaporated, and the residue was dissolved in the ethyl acetate washings. The solution was washed sequentially with 1 M hydrochloric acid (2×600 mL), water (2×300 mL), dilute sodium carbonate solution (saturated: H$_2$O, 1:1, 2×600 mL), water (2×300 mL) and saturated sodium chloride solution (300 mL). The organic layer was separated, dried over sodium sulfate, and the solvent was removed under vacuum. 4-formyl-N,N-diethylbenzamide (117.14 g) was obtained as a light yellow oil, which was used without further purification (85% unchromatographed yield). $^1$H NMR (300 MHz, CDCl$_3$): δ 1.09-1.25 (m, 6H); 3.19-3.31 (d, J=6.4 Hz, 2H); 3.54-3.56 (d, J=6.6 Hz, 2H); 7.49-7.52 (d, J=8.1 Hz, 2H); 7.89-7.92 (d, J=8.2 Hz, 2H); 9.98 (s, 1H).

3-Iodophenol (110 g, 500 mmol) and imidazole (93.6 g, 1735 mmol, 2.75 equivalents) were placed in 1150 mL of dry dichloromethane in a 2000 mL flask and cooled to 15° C. in an ice/water bath under nitrogen. t-Butyldimethylsilyl chloride (82.9 g, 550 mmol) in 200 mL of dry dichloromethane was added dropwise through an addition funnel to the reaction. The reaction mixture was stirred under nitrogen overnight and filtered, washing with dichloromethane. The combined extracts were washed with water (400 mL), 0.5 N NaOH solution (600 mL), and water (2×300 mL). The organic layer was dried over $Na_2SO_4$/NaCl and evaporated to yield a light yellow oil (166 g).

3-Iodophenoxy-tert-butyldimethylsilane (48.85 g, 146 mmol) was placed in a 250 mL flask with 180 mL of dry tetrahydrofuran at room temperature under nitrogen, Isopropylmagnesium chloride (73 mL, 146 mmol, 2.0 M solution in tetrahydrofuran) was added through an addition funnel to form a light yellow solution. The reaction was stirred at room temperature for 1 hour. In the meantime, 30 g of 4-formyl-N,N-diethylbenzamide was dissolved in 300 mL of dry tetrahydrofuran in another 1000 mL flask and cooled to −72° C. under nitrogen. The freshly prepared 3-phenoxy-tert-butyl-dimethylsilane magnesium chloride was slowly added into the 1000 mL flask. The transfer rate was monitored to maintain reaction temperature below −70° C. The reaction was allowed to warm to room temperature while stirring overnight. The mixture was quenched with 24 mL of saturated aqueous ammonium chloride, diluted with 600 mL of diethyl ether, and washed with 600 mL of water followed by 150 mL of saturated sodium chloride. The ethereal solution was dried over sodium sulfate and the solvent was removed to give crude 4-{[3-(tert-butyl-dimethylsilanyloxy) phenyl]hydroxymethyl}-N,N-diethylbenzamide as a yellow oil. Crude yield was~100%. The crude product was slurried in a solution of 20% ethyl acetate in pentane. The resulting white precipitate was collected by filtration, washed with pentane, and dried overnight (30 mmHg, 40° C.).

The 4-{[3-(tert-butyldimethylsilanyloxy)phenyl]hydroxymethyl}-N,N-diethylbenzamide (50 g, 120.9 mmol) was dissolved in 800 mL of dichloromethane and 13.23 mL (181.3 mmol) of thionyl chloride was added dropwise. The reaction solution was stirred at room temperature for 5 hours and the solvent was removed under vacuum. The residual yellow oil was purified by chromatography on silica gel (17% EtOAc in pentane, then 30% EtOAc in pentane) to give 22.58 g (52.26 inmol) of the desired product as a yellow oil.

The pure 4-{[3-(tert-butyldimethylsilanyloxy)phenyl] chloromethyl}-N,N-diethyl-benzamide (22.58 g, 52.26 mmol) was dissolved in 350 mL of dry acetonitrile. Sodium iodide (7.83 g, 52.26 mmol), diisopropylethylamine (13.69 mL, 78.39 mmol), and (2R, 5S)-1-allyl-2,5-dimethylpiperazine (8.06 g, 52.26 mmol) were added. The mixture was stirred at reflux, under nitrogen, for 3 hours. The acetonitrile was removed under reduced pressure and the reaction mixture was poured into etnyl acetate (400 mL) and potassium carbonate solution (150 mL of a 2M aqueous solution). The organic layer was separated, washed with water and brine, dried over solid potassium carbonate, and concentrated in vacuo. Crude product (30 g) was obtained as a dark brown oil with a crude yield~100%.

The crude product was purified by chromatography on silica gel to give the two benzhydryl epimers. Elution was performed first with 20% EtOAc in pentane, followed by stepwise portions of 30%, 40%, 50% and 80% EtOAc in pentane to give 11.00 g (20.00 mmol) of 4-{(R)-((2S,5R)-4-allyl-2,5-dimethylpiperazin-1-yl)[3-(tert-butyl-dimethyl-silanyloxy)phenyl]methyl}-N,N-diethylbenzamide as a yellow oil and 9.27 g of 4-{(S)-((2S,5R)-4-allyl-2,5-dimethylpiperazin-1-yl)[3-(tert-butyl-dimethylsilanyloxy)-phenyl]methyl}-N,N-diethylbenzamide (16.86 mmol, yellow oil). The isomers were identified by TLC comparison to the known pure isomer described in Example 1.

The 4-{(S)-(2 S,5R)-4-allyl-2,5-dimethylpiperazin-1-yl) [3-(tert-butyldimethylsilanyloxy)phenyl]methyl}-N,N-diethylbenzamide (9.27 g, 16.86 mmol) was dissolved in 35 mL of dry acetonitrile followed by tetraethylammonium fluoride dihydrate (4.69 g, 25.29 mmol) and stirred overnight. The reaction solution was concentrated to dryness, the residue was dissolved in 40 mL of ethyl acetate and extracted with 2% aqueous $NaHCO_3$ solution (3×40 mL) and water (40 mL). The organic layer was dried over sodium sulfate and evaporated to give 8.55 g of 4-{(S)-(2S,5R)-4-allyl-2,5-dimethylpiperazin-1-yl)[3-hydroxyphenyl]methyl}-N,N-diethylbenzamide as a red amorphous solid.

The allyl group was removed using $Pd(dba)_2$/DPPB in the presence of thiosalicylic acid by the method of Genet as discussed in Example 1. The reaction was concentrated and the residue was poured into 200 mL ethyl acetate and 300 mL diethyl ether. After washing with 340 mL of water, the organic solution was extracted with 10% citric acid (5×80 mL). The combined acid extracts were filtered to remove a small amount of suspended solid and the pH was adjusted to 8-8.5 using 15% NaOH solution. The resulting oily suspension was extracted with dichloromethane (3×300 mL). The combined organic solution was dried ($Na_2SO_4$/$MgSO_4$) and concentrated under reduced pressure. The residue was a pale orange solid.

The 4-[(S)-((2S,5R)-2,5-dimethylpiperazin-1-yl)(3-hydroxyphenyl)methyl]-N,N-diethylbenzamide (0.51 g, 1.29 mmol) was dissolved in 10 mL of dry acetonitrile. Sodium iodide (20 mg, 0.13 mmol) was added and the reaction was stirred under nitrogen at room temperature during the addition of triethylamine (0.72 mL, 5.16 mmol), followed by methyl 4-(bromomethyl)benzoate (0.59 g, 2.58 mmol). The reaction mixture was stirred under nitrogen overnight. The solvent was removed by evaporation and the residue was partitioned between ethyl acetate and saturated sodium bicarbonate solution. The organic layer was washed with water, dried over $Na_2SO_4$/$MgSO_4$ and concentrated under reduced pressure. The residual light yellow oil was purified by chromatography on silica gel (50% EtOAc in $CH_2Cl_2$) to give 0.45 g (0.83 mmol) of methyl 4-{(2R, 5S)-4-[(S)-(4-diethylcarbamoylphenyl)(3-hydroxyphenyl)methyl]-2,5-dimethyl-1-piperazinylmethyl}-benzoate as a white amorphous solid.

The hydrolysis of the above ester was done with 1 mL of 10% NaOH solution in 3 mL of ethanol. The reaction mixture was evaporated to dryness and 2 mL of water was added. The solution was extracted with 2 mL of EtOAc/$Et_2O$ twice to remove impurities, then 1 M HCl was added dropwise to the precipitation point at pH 4-4.5. A white gel was formed and collected by filtration, washing with a small volume of cold water. The 4-{(2R,5S)-4-[(S)-(4-diethylcarbamoylphenyl)(3-hydroxyphenyl)methyl]-2,5-dimethylpiperazin-1-ylmethyl}benzoic acid was dried in a vacuum oven (30 mmHg, 40° C.) to give 180 mg of white solid. $^1$H NMR (300 MHz, d$_6$-DMSO): δ 0.98-1.16 (m, 12H); 1.89-2.05 (m, 2H); 2.48-2.65 (m, 5H); 3.10-3.50 (m, 5H); 3.76-3.80 (d, J=13.9 Hz, 1H); 4.94 (s, 1H); 6.53-6.95 (d, J=8.0 Hz, 1H); 6.75-6.85 (m, 2H); 7.02-7.09 (t, 1H); 7.29-7.40 (m, 6H); 7.80-7.84 (d, J=8.3 Hz, 2H); 9.29 (s, 1H).

EXAMPLE 3

3-{(2R, 5S)-4-[(R)-(4-Diethylcarbamoylphenyl)(3-hydroxyphenyl)methyl]-2,5-dimethyl-1-piperazinylmethyl}benzoic acid

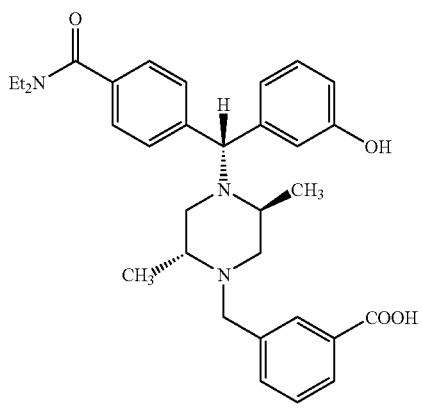

4-{(R)-(2S,5R)-4-Allyl-2,5-dimethyl-piperazin-1-yl)-[3-(tert-butyldimethylsilanyloxy)-phenyl]methyl}-N,N-diethylbenzamide (11.00 g, 20.0 mmol, Example 2) was dissolved in 40 mL of dry acetonitrile and tetraethylammonium fluoride dihydrate (5.56 g, 30.00 mmol) was added and stirred overnight. The reaction solution was concentrated to dryness, the residue was dissolved in 40 mL of ethyl acetate and washed with 2% aqueous NaHCO$_3$ solution (3×40 mL) and water (40 mL). The organic layer was dried over sodium sulfate and evaporated to give 4-{(R)-(2S,5R)-4-allyl-2,5-dimethylpiperazin-1-yl)[3-hydroxyphenyl]methyl}-N,N-diethylbenzamide (10.30 g) as a yellow amorphous solid.

The allyl group was removed using Pd(dba)$_2$/DPPB in the presence of thiosalicylic acid by the method of Genet as discussed in Example 1. The reaction was concentrated and the residue was poured into 200 mL ethyl acetate and 300 mL diethyl ether. After washing with 340 mL of water, the organic solution was extracted with 10% citric acid (5×80 mL). The combined aqueous extracts were filtered to remove a small amount of suspended solid and the pH was adjusted to 8-8.5 using 15% NaOH solution. The resulting oily suspension was extracted with dichloromethane (3×300 mL). The combined organic extracts were dried (Na$_2$SO$_4$/MgSO$_4$) and concentrated under reduced pressure. The residue was a pale orange solid.

The 4-[(R)-((2S,5R)-2,5-dimethylpiperazin-1-yl)(3-hydroxyphenyl)methyl]-N,N-diethylbenzamide (2.50 g, 6.32 mmol) and 3-carboxybenzaldehyde (1.90 g, 12.64 mmol) were placed in a 250 mL flask with 60 mL of tetrahydrofuran and 0.80 mL (13.91 mmol) of acetic acid. The reaction was stirred at room temperature for 20 minutes, and sodium triacetoxyborohydride (2.68 g, 12.64 mmol) was added portionwise. The reaction solution became very turbid and was sealed under nitrogen and stirred overnight. The reaction mixture was evaporated to dryness and partitioned between ethyl acetate (60 mL) and 3M HCl (12 mL). The organic layer was extracted with a further 5×12 mL 3M HCl. The combined aqueous extracts were adjusted to pH 4.5-5 with 0.5 M NaOH solution and solid Na$_2$CO$_3$ The resulting gel was collected by filtration, dissolved in 30 mL of 0.5 M NaOH solution, and extracted with 20 mL of EtOAc/Et$_2$O twice to remove impurities. 1M HCl was added dropwise to the aqueous solution to the precipitation point at pH 4.5-5. The resulting white gel was collected by filtration and washed with a small volume of cold water. The 3-{(2R,5S)-4-[(R)-(4-diethylcarbamoylphenyl)-(3-hydroxyphenyl)methyl]-2,5-dimethylpiperazin-1-ylmethyl}benzoic acid was dried in a vacuum oven (30 mmHg, 40° C.) to give 1.55 g of white solid. $^1$H NMR (300 MHz, d$_6$-DMSO): δ 0.99-1.20 (m, 12H); 1.89-2.05 (m, 2H); 2.48-2.65 (m, 5H); 3.06-3.57 (m, 5H); 3.78-3.83 (d, J=12.5 Hz, 1H); 4.94 (s, 1H); 6.63-6.84 (m, 3H); 7.09-7.91 (m, 9H); 9.36 (s, 1H).

EXAMPLE 4

The compound of formula (3) (hereinafter Compound 1) as identified above, was evaluated for in vitro opioid receptor activity in the mouse vas deferens (Mouse Vas Deferens ED$_{50}$) receptor system. The assay procedure used for such determination of receptor activity is set out below.

In vitro bioassays: Vasa deferentia (MVD), CD-1 strain, (Harlan, Raleigh, N.C.) were removed from mice and suspended between platinum electrodes with 0.5 g of tension in organ bath chambers containing a modified Mg++ free Krebs buffer of the following composition (millimolar): NaCl, 117.5; KCl, 4.75; CaCl$_2$, 2.6; KH$_2$PO$_4$, 1.20; NaHCO$_3$, 24.5; and glucose, 11. The buffer was saturated with 95% O$_2$/5% CO$_2$ and kept at 37° C. Tissues were stimulated at supramaximal voltage with 10-Hz pulse trains for 400-msec.; train interval 10 seconds; and 1.0 msec pulse duration at maximal voltage. Delta receptor activity was determined, in the presence of 1 uM CTOP (a highly selective mu antagonist; K. Gulya, J. T. Pelton, V. J. Hruby and H. I. Yamamura, *Life Sci.* 38: 2221-2229, (1986)) and 15 nM nor-BNI (a selective kappa antagonist; P. S. Portoghese, A. W. Lipkowski, and A. E. Takemori, *Life Sci.* 40, 1287 (1987)) by adding appropriate concentrations of the test compound to organ baths and allowing a maximal response before addition of the next higher concentration. Mu receptor activity was determined in similar fashion, but in the presence of 3 μM TIPP (a highly selective delta antagonist; P. W. Schiller, T. M.-D. Nguyen, G. Weltrowska, B. C. Wilkes, B. J. Marsden, C. Lemieux, and N. N. Chung, *Proc. Natl. Acad. Sci.* 89, 11871 (1992)) and 15 nM selective kappa antagonist nor-BNI.

Kappa receptor activity was determined in the presence of 1 uM highly selective mu antagonist CTOP and 3 uM highly selective delta antagonist TIPP.

The inhibition percentage of the electrically induced muscle contractions was determined for the compound at varying cumulative concentrations. The $ED_{50}$ values were extrapolated from curves showing the dose concentration plotted against the response (J. A. H. Lord, A. A. Waterfield, J. Hughes, H. W. Kosterlitz, Nature 267, 495, (1977)). The results are set forth below in Table 1.

TABLE 1

| Compound | Structure | Mouse Vas Deferens $ED_{50}$ (nM) | | |
| --- | --- | --- | --- | --- |
| | | μ | δ | κ |
| 1 | 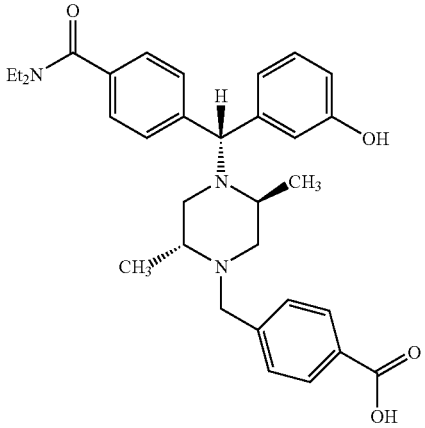 | >1000 | 17.3 | 10870 |

EXAMPLE 5

Compound 1 was also evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, Ark.). Tissues were homogenized in 50 mM TRIS (Tris[hydroxymethyl]aminomethane) buffer (pH 7.4) containing 50 μg/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

Radioligand binding assays were performed in 10 mM TRIS buffer (pH 7.4) containing 50 μg/ml soybean trypsin inhibitor, 1 mM EDTA, 5 mM $MgCl_2$, and 100 μM PMSF. Tritium-labeled DAMGO (μ), Deltorphin II (δ), or U69593 (κ) purchased from New England Nuclear were used as ligands in competitive experiments ($2-3\times10^{-10}$ M final concentrations) with non-specific binding defined by $0.5\times10^{-6}$ M Naloxone (purchased from SIGMA Chemical Co.). All binding assays were run at room temperature for 90 minutes and then terminated by rapid filtration on GF/C glass fiber filters (Whatman, Hillsboro, Oreg.) with 50 mM TRIS buffer (4° C., pH 7.4) employing a Brandel Semi-automatic Cell Harvester (Model M48, Brandel, Gaithersburg, Md.). The filters were washed twice with 50 mM TRIS buffer (4° C., pH 7.4) and the filters were placed in liquid scintillation cocktail and the bound radioactivity counted on a Beckman LS 6500 scintillation counter. The potency of the compound (1) of formula (3) in inhibiting the binding of radiolabelled DAMGO (μ), Deltorphin II (δ), or U69593 (κ) was determined from full concentration-effect curves. With the computer program Prism (GraphPad Software Inc., San Diego, Calif.) the $IC_{50}$ values were determined using a one-site nonlinear regression analysis of the radioligand binding data. The $IC_{50}$ values were then converted to $K_i$ values using the Cheng-Prusoff equation. (Cheng Y and Prusoff W H (1973), Relationship between the inhibition constant (Ki) and the concentration of inhibitor which causes 50 percent inhibition ($I_{50}$) of a enzymatic reaction; Biochem Pharm., 22:3099-3108.).

The results of the radioligand binding assays are set forth below in Table 2:

TABLE 2

| Compound # | Structure | Rat Brain Membrane $K_i$ (nM) | | Guinea Pig Brain Membrane $K_i$ (nM) |
|---|---|---|---|---|
| | | μ | δ | κ |
| 1 | [structure: Et₂N-C(O)-phenyl-CH(3-hydroxyphenyl)-N(piperazine with 2,5-diCH₃)-CH₂-phenyl-COOH] | 1519 | 1.89 | 17,360 |

Results: It is evident that compound (1) of formula (3) exhibits distinct and different binding affinity for the different types of receptors tested. The strong affinity of the compound for the delta receptor is shown by the very low concentration required to inhibit the binding of the labeled compounds.

EXAMPLE 6

Analgesia was assayed in rats using the tail pinch test. Compound 1 was administered intravenously. Nociceptive response values were obtained for a 1-2 hour period. An artery clamp was placed on the tail (one inch from the tip of the tail) for a short duration until an escape response occurred (i.e. tail-flick or vocalization). The escape response latency was recorded by means of a stopwatch. A cutoff time of 20 sec. was used to prevent unnecessary tissue damage.

Rats were observed for nociceptive responses of vocalization or painful body movements. The elapsed time to elicit a pain response was recorded as the tail pinch latency in seconds.

The ED50 values for analgesia potency for the analgesic potency (half maximum effective dose, ED50) was determined by the dose at which half of the animals did not show any nociceptive response to the artery clamp pressure within 20 seconds. As shown in Table 3, Compound 1 showed no analgesic activity, thus indicating that the tested compound does not cross the blood brain barrier and is considered a non-analgesic compound. Further, the compound acts predominately at peripheral delta opioid receptors. More important, even at the high dose of 50 mg/kg no seizures were observed in any of the test animals indicating that compound (1) is restricted to essentially peripheral delta receptors.

TABLE 3

| Compound | Structure | Analgesia $ED_{50}$ mg/kg | Seizures |
|---|---|---|---|
| 1 | [structure: Et₂N-C(O)-phenyl-CH(3-hydroxyphenyl)-N(piperazine with 2,5-diCH₃)-CH₂-phenyl-COOH] | >50 | NONE |

EXAMPLE 7

Compound 1, at concentrations of 1 nM, 2 nM and 10 nM was administered at approximately 15 minutes prior to occlusion of the left anterior descending (LAD) coronary artery in hearts isolated from Sprague-Dawley rats. The isolated hearts were perfused retrograde with oxygenated Krebs-Henseleit buffer through the aorta in the Langendorff fashion. Infarction was induced by 35 min of regional ischemia followed by 120 min of reperfusion. A 6-0 suture was passed around the main branch of the (LAD) coronary artery to make a snare.

Regional ischemia was induced by tightening the snare around the LAD. After an ischemic period of 35 min, the snare was loosened and the hearts reperfused with oxygenated physiologic buffer for 120 min. The LAD occluder was retightened at the end of reperfusion and 0.125% Evans blue in saline was injected into the heart through the aorta for visualization of the non-ischemic zone. The heart tissue was then sliced and infarct size was assessed following staining for 15 min with 1.5% triphenyltetrazolium chloride (TTC) in physiologic buffer. After fixation in 10% buffered formalin, the slices were mounted between glass slides and images were acquired digitally using a scanner. The images were processed using Adobe Photoshop 5.0. Using Optimas 6.2 image analysis software, the non-ischemic zone, area at risk, and the infarct were quantitated using computerized planimetry.

Figure 1B:
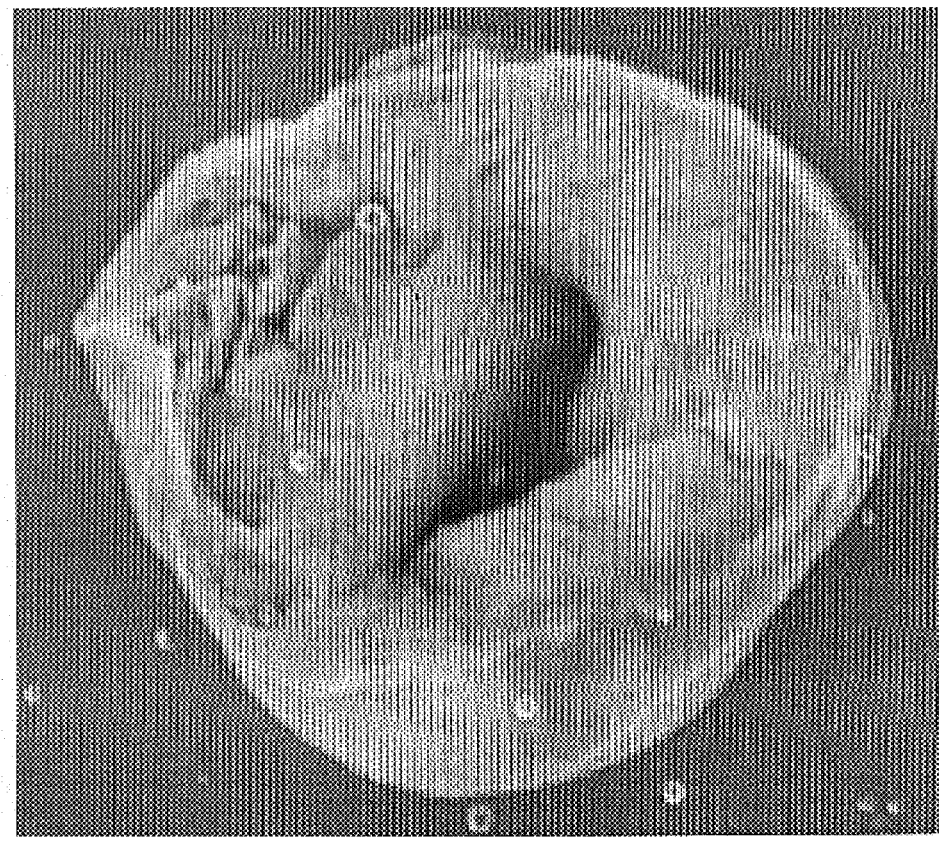

The results of one such group are shown in FIG. 1, which illustrates a histological staining slide of the infarct size in excised heart tissue from a control and treated animal after acute treatment with 1 nM of Compound 1. It was found that pretreatment reduced the infarct size by 71% relative to that of the control group.

Table 4 shows the decrease in ischemic damage as a percent of area at risk (%IS/AAR) produced by Compound 1 in this preparation.

TABLE 4

| Concentration (nM Compound 1) | % IS/AAR |
| --- | --- |
| Control | 55 ± 1 |
| 1 | 18 ± 5 |
| 2 | 9 ± 2 |
| 10 | 20 ± 6 |

Under control conditions 35 minute regional ischemia induces cellular damage in 54.7±1.2% of the area at risk. Maximal protection was produced by 2 nM Compound 1, protecting against almost 90% of the damage present in the control group.

Hemodynamic parameters measured after 35 min regional ischemia, and 120 minutes of reperfusion are set forth below in Table 5.

TABLE 5

| Amount of Compound 1 (nM) | HRXDP % inhibition | +dP/dt % inhibition | −dP/dt % inhibition | CF % inhibition |
| --- | --- | --- | --- | --- |
| Control | 61.8 | 54.2 | 54.8 | 59.7 |
| 0.1 nM | 32 | 26 | 19 | 43 |
| 1.0 nM | 17 | 7 | 10 | 13 |
| 10 nM | 32 | 21 | 18 | 38 |

HRXDP, heart rate × developing pressure;
+dP/dt, inotropy;
−dP/dt, lustitropy;
CF, coronary flow The results of the hemodynamic parameters show that without pharmacological pretreatment there is a 61.8% inhibition in the HRXDP parameter and at least a 50% inhibition in contracting and relaxing pressure with reduced coronary flow. In contrast, if the animal was pretreated with Compound 1 of the present invention, the heart parameters were greatly improved. On the average, the heart tissue is functioning in the range of at least 75% and in some parameters up to 90% of normal. These results show that administration of Compound 1 can confer cardioprotection when administered prior to an ischemic event.

EXAMPLE 8

Anesthesia was produced in test animals (rats) by an intraperitoneal injection of pentobarbital sodium. A midline incision was made with reflection of the skin over from the midsternal line. Ventilation was provided by a rodent ventilator (Harvard rodent ventilator) with room air mixed with oxygen. Normal chest expansion was noted as seen with a conscious rat. Delicate dissection was required and the chest was opened by a lateral cut with sternotomy scissors along the left side of the sternum cutting through ribs to approximately midsternum. Delicate dissection was needed at the head of the sternum to avoid large bilateral venous confluences. The chest was retracted by use of 5-0 silk or monofilament suture. Ligation proceeded with 7-0 silk suture passed with a tapered needle underneath the left anterior branch of the coronary artery 1-3 mm from the tip of the normally positioned left auricle. A 1-mm section of PE-10 tubing was placed on top of the vessel, and a knot was tied on top of the tubing to occlude the coronary artery. After occlusion for 35 min, reperfusion occurred by cutting the knot on top of the PE-10 tubing with a number 11 surgical blade. Compound 1 was administered intravenously at 0.1 mg/kg or 1.0 mg/kg 15 min prior to ligation of the LAD coronary artery. The infarct size was determined by Evans blue and TTC staining 2 hrs, 24 hrs, and 167 hrs following ischemia and reperfusion.

Compound 1 was dissolved in 0.9% saline and injected into the test animals. The LAD coronary artery was reoccluded and Patent blue dye was injected into the venous catheter to stain the normally perfused region of the heart. The heart was excised and the left ventricle removed and sliced into cross-sectional pieces. This procedure allowed for visualization of the normal, nonischemic region, the area at risk and the infarction size. TTC was used as an indicator to separate out viable and nonviable tissue (Klein, H. H., et al., Virchows Arch (1981) 393:287-297). The tissue was stored overnight in a 10% formaldehyde solution. The following day, the infarct size (IS) was calculated as a percentage (%) of the area at risk using digital imaging techniques as described in Example 7.

It was found that infarct size was significantly smaller in the rats that were pretreated with Compound 1 relative to the control group as shown in Table 6.

TABLE 6

| Time of Measurement of Infarct Size | Reduction of Infarct Size Relative to Non treated Control |
|---|---|
| Measurement after acute administration of 1 mg/kg of Compound 1 | 48% |
| Measurement taken 156 hours after administration of 1 mg/kg of Compound 1 | 43% |

Pretreatment with Compound 1 showed a 48% reduction in the infarct size relative to the control group after acute administration. At approximately 7 days after the initial treatment a 43% reduction was still exhibited in the infarct size relative to the non-treated control group.

EXAMPLE 9

Male rats were anesthetized with Inactin (Thiobutabarbital sodium salt, 178 mg/kg i.p.) or Urethane (1.2 g/kg i.p.). When a surgical plane was achieved a tracheotomy was performed (pe-240 tubing) and the animal was catheterized with pe-50 tubing in the jugular vein (for i.v. compound and dye administration) and carotid artery (for measurement of blood pressure), then the animal placed on a ventilator (Harvard, model 683) attached to an $O_2$ source and respirated at 36-42 bpm. The carotid artery catheter was connected to a PT300 pressure transducer via a 3-way syringe valve for measurement of arterial blood pressure and heart rate. After the animal had stabilized a small blood sample (150 microliters) was drawn from the carotid catheter for blood gas analysis.

A left thoracotomy was performed at the $5^{th}$ intercostal space followed by a pericardiotomy and adjustment of the left atrial appendage to reveal the location of the left coronary artery. A ligature (6-0 prolene) was passed below the left atrial appendage to the right portion of the left ventricle. The ends of the suture were threaded through a polyethylene tube that had been flanged on one end (such that the flanged end was proximal to the ventricular wall) to form a snare. The coronary artery was occluded by pulling the suture taut and clamping the snare onto the epicardial surface with a hemostat. Coronary artery occlusion was verified by epicardial cyanosis and blood pressure decrease. Occlusion was held for 30 minutes. Reperfusion was initiated by un-clamping the snare and confirmed by visualizing an epicardial hyperemic response. The period of reperfusion was 1.5-2 hours. At the end of the reperfusion period the coronary artery was again occluded using the snare and Patent Blue dye (0.4 ml of 10% w/v in saline) was injected via the i.v. catheter. The heart was immediately removed after the dye had spread through the circulation. The atria and right ventricle were rapidly removed and the remaining left ventricle, sectioned into 4-5 slices. The areas defined as normal (dyed blue) were separated from the area at risk (AAR, not dyed blue) and the tissue put into separate 20 ml vials containing 100 mM $KH_2PO_4$ and 0.187% 2,3,5-Triphenyltetrazolium chloride (TTC) and incubated at 37° C. for 5-10 minutes. Tissues were then placed in separate vials containing a 10% buffered formaldehyde solution overnight for fixing. Infarcted areas were then dissected from non-infarcted areas. Normal; AAR, non-infarcted; and infarcted tissue were measured gravimetrically.

Compound 1 was injected at doses ranging from 0.01 mg/kg to 1.0 mg/kg via the i.v. catheter 5 minutes prior to LAD occlusion (pre-ischemic administration).

The results from two separate studies are presented in Table 7 below.

TABLE 7

| Drug Treatment (mg/kg Compound 1) | Study 1 (% IS/AAR) | Study 2 (% IS/AAR) |
|---|---|---|
| Control | 54 ± 10 | 54 ± 3 |
| 0.01 | 56 ± 5 | |
| 0.03 | 44 ± 10 | 40 ± 3 |
| 0.1 | | 39 ± 3 |
| 0.3 | 35 ± 11 | 38 ± 3 |
| 1.0 | 40 ± 8 | |

Administration of Compound 1 produced clear protective effects in both studies tested up to doses of 1.0 mg/kg. Control groups indicated ischemic damage of ~50-55% of the area at risk (AAR). Compound 1, administered at doses higher than 0.1 protected against between about 30 and 40% of this damage across both studies.

EXAMPLE 10

The identical experimental method was used as described in Example 9 except that Compound 1 was administered immediately prior to the release of the ligature occluding the LAD (i.e. immediately after initial ischemic damage and prior to reperfusion). Compound 1 was tested at 0.3 mg/kg in this model and clear protective effects were demonstrated.

Control ischemic damage was ~50% of the area at risk, as with the control groups in Example 9. However, Compound 1 protected against 30-40% of this damage when administered at the time of reperfusion injury, as opposed to prior to ischemic damage as described in Example 9.

While the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

What is claimed is:

1. A method of reducing ischemic damage in cardiac tissue in a subject comprising:
  administering to the subject in need thereof an effective amount of a composition comprising a non-analgesic diarylmethylpiperazine compound of the general formula:

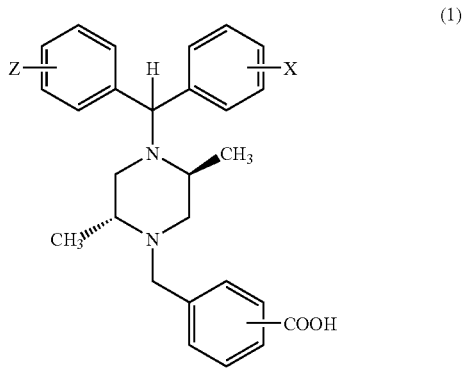

(1)

wherein:
Z is selected from the group consisting of:
hydrogen;
halogen;
$C_1$-$C_6$ alkyl, $C_2$-$C_6$ alkenyl, $C_2$-$C_6$ alkynyl;
$C_1$-$C_6$ haloalkyl;
$C_1$-$C_6$ alkoxy;
$C_3$-$C_6$ cycloalkoxy;
sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and an $C_1$-$C_6$ alkyl moiety, or $C_5$-$C_{10}$ aryl;
sulfoxides of the formula $SOR^8$ where $R^8$ is the same as above;
sulfones of the formula $SO_2R^8$ where $R^8$ is the same as above;
nitrile;
$C_1$-$C_6$ acyl;
alkoxycarbonylamino (carbamoyl) of the formula $NHCO_2R^8$ where $R^8$ is the same as above;
carboxylic acid, or an ester, amide, or salt thereof;
aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C;
carboxamides of the formula $CONR^9R^{10}$ where $R^9$ and $R^{10}$ are the same as above, or $C_2$-$C_{30}$ peptide conjugates thereof; and
sulfonamides of the formula $SO_2NR^9R^{10}$ where $R^9$ and $R^{10}$ are the same as above; and
X is selected from the group consisting of hydrogen, hydroxyl, halogen and alkoxy,
or a pharmaceutically acceptable ester or salt thereof.

2. A method of reducing ischemic damage in cardiac tissue in a subject comprising: administering to the subject in need thereof an effective amount of a therapeutic composition comprising a non-analgesic diarylmethylpiperazine compound of the formula:

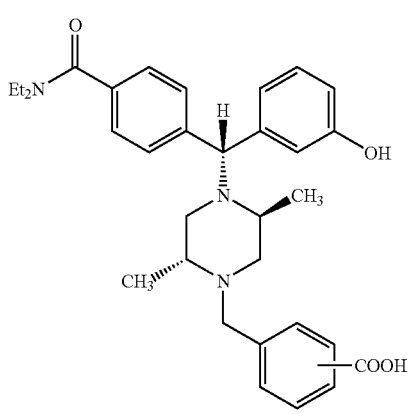

(2)

or a pharmaceutically acceptable salt or ester thereof.

3. A method of reducing ischemic damage in cardiac tissue in a mammal, the method comprising: administering to the mammal in need thereof an effective amount of a non-analgesic diarylmethylpiperazine compound of the formula:

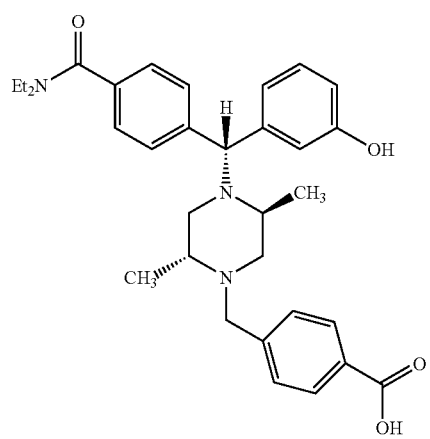

or a pharmaceutically acceptable salt or ester thereof.

4. The method according to claim 3, wherein the diarylmethylpiperazine compound is administered multiple times concurrently with the onset of an ischemic event.

5. The method according to claim 3, wherein the diarylmethylpiperazine compound is administered to the mammal to reduce cardiac tissue damage in an individual in a symptomatic phase of ischemic heart disease.

6. The method according to claim 3, wherein the diarylmethylpiperazine compound is administered after the onset of an ischemic event.

7. The method according to claim 3, further comprising administering a second compound that effectuates a corrective cardiac response.

8. The method according to claim 7, wherein the second compound is selected from the group consisting of nitrates, beta-adrenergic blockers, calcium channel antagonists, ACE inhibitors, non-peptide angiotensin II antagonists, IIb/IIIa antagonists and aspirin.

9. The method according to claim 7, wherein the second compound is administered contemporaneously with the diarylmethylpiperazine compound.

10. The method according to claim 3, wherein the diarylmethylpiperazine compound is administered by a mode of administration selected from the group consisting of parenteral, non-parenteral, oral, rectal, topical, nasal, ophthalmic, subcutaneous, intramuscular, intravenous, transdermal, spinal, intrathecal, intra-articular, intra-arterial, subarachnoid, sublingual, oral mucosal, bronchial, lymphatic, and intra-uterine administration.

11. The method according to claim 3, wherein the mammal is a human.

12. A method of treating ischemia and reperfusion injury in cardiac tissue in a mammal comprising administering to the mammal in need thereof an effective amount of a non-analgesic delta opioid receptor agonist of the formula:

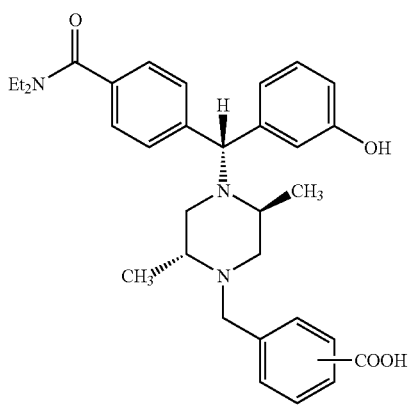

(2)

or pharmaceutically acceptable esters and salts thereof in combination with a second compound that effectuates an anti-ischemic effect.

13. The method of claim 12, wherein the second compound is arginine hydrochloride.

14. A method of effectuating ischemic preconditioning of cardiac tissue in a subject in need thereof, the method comprising: administering to the subject an effective amount of a non-analgesic diarylmethylpiperazine compound of the formula:

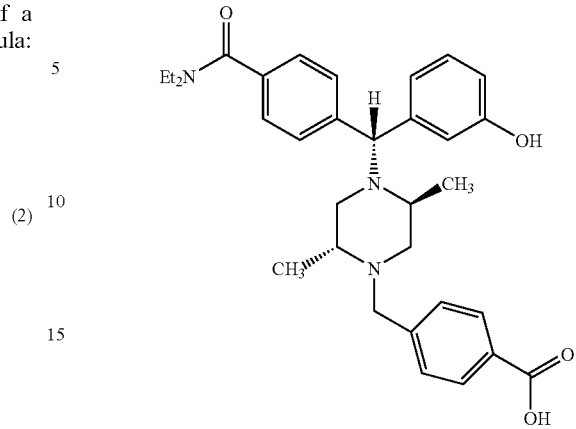

or pharmaceutically acceptable esters and salts thereof.

15. The method of claim 14, wherein the compound is administered by a mode of administration selected from the group consisting of parenteral, non-parenteral, oral, rectal, topical, nasal, ophthalmic, subcutaneous, intramuscular, intravenous, transdermal, spinal, intrathecal, intra-articular, intra-arterial, sub-arachnoid, sublingual, oral mucosal, bronchial, lymphatic, and intra-uterine administration.

16. The method according to claim 14, further comprising administering a second compound that effectuates a corrective cardiac response.

17. The method according to claim 16, wherein the second compound is selected from the group consisting of nitrates, beta-adrenergic blockers, calcium channel antagonists, ACE inhibitors, non-peptide angiotensin II antagonists, IIb/IIIa antagonists and aspirin.

18. The method according to claim 16, wherein the second compound is administered contemporaneously with the diarylmethylpiperazine compound.

* * * * *

UNITED STATES PATENT AND TRADEMARK OFFICE
CERTIFICATE OF CORRECTION

PATENT NO.         : 7,314,880 B2                                        Page 1 of 1
APPLICATION NO. : 10/749437
DATED              : January 1, 2008
INVENTOR(S)        : Chang et al.

It is certified that error appears in the above-identified patent and that said Letters Patent is hereby corrected as shown below:

Column 12, Line 54: "3-hydroxybenyl" should be --3-hydroxyphenyl--

Column 15, Line 51: "inmol" should be --mmol--

Column 15, Line 61: "etnyl" should be --ethyl--

Column 18, Line 6: "mntrogen" should be --nitrogen--

Signed and Sealed this

Twelfth Day of August, 2008

JON W. DUDAS
*Director of the United States Patent and Trademark Office*